United States Patent [19]

Pandya et al.

[11] Patent Number: 5,837,286

[45] Date of Patent: Nov. 17, 1998

[54] TASTE MASKING FOR UNPLATABLE FORMULATIONS

[76] Inventors: Harish B. Pandya, 11 Floral Dr., Randolph, N.J. 07869; Thomas P. Callahan, 705 Lindsley Dr. AB#1-K, Morristown, N.J. 07960

[21] Appl. No.: 782,433

[22] Filed: Jan. 15, 1997

[51] Int. Cl.[6] ...................................................... A61K 9/46
[52] U.S. Cl. ........................ 424/466; 514/849; 514/853
[58] Field of Search ..................................... 424/440, 466; 514/855, 849, 853

[56] References Cited

U.S. PATENT DOCUMENTS

| | | |
|---|---|---|
| 2,151,517 | 3/1939 | Kamlet . |
| 2,397,799 | 4/1946 | Martin et al. . |
| 2,421,714 | 6/1947 | Rieveschl, Jr. . |
| 2,427,878 | 9/1947 | Rieveschl . |
| 3,028,429 | 4/1962 | Wilbert et al. . |
| 3,495,001 | 2/1970 | Leonards . |
| 3,518,344 | 6/1970 | Welsh et al. . |
| 4,083,950 | 4/1978 | Duvall et al. . |
| 4,642,903 | 2/1987 | Davies . |
| 4,783,331 | 11/1988 | Alexander et al. . |
| 4,942,039 | 7/1990 | Duvall et al. ............................ 424/466 |
| 5,037,657 | 8/1991 | Jones et al. .............................. 424/466 |
| 5,085,853 | 2/1992 | Williams et al. . |
| 5,100,652 | 3/1992 | Kross et al. . |
| 5,171,571 | 12/1992 | Stephan et al. ......................... 424/466 |
| 5,174,990 | 12/1992 | Douglas . |
| 5,178,878 | 1/1993 | Wehling et al. . |
| 5,186,926 | 2/1993 | Williams et al. . |
| 5,223,264 | 6/1993 | Wehling . |
| 5,225,197 | 7/1993 | Bolt et al. . |
| 5,244,651 | 9/1993 | Kayane et al. . |
| 5,501,858 | 3/1996 | Fuisz . |
| 5,628,986 | 5/1997 | Sanker et al. . |

FOREIGN PATENT DOCUMENTS

| | | |
|---|---|---|
| 0241804 | 10/1987 | European Pat. Off. . |
| 0455599 | 11/1991 | European Pat. Off. . |
| WO 9428872 | 12/1994 | WIPO . |

*Primary Examiner*—Bernard Lipman
*Assistant Examiner*—N. Sarofim
*Attorney, Agent, or Firm*—Mary G. Boguslaski

[57] ABSTRACT

This invention provides a taste masking composition composed of clove oil and either supportive flavor components or calcium carbonate. This taste masking composition has been found to be particularly useful to mask unpalatable medicinals in formulations which are intended to be chewed, dissolve in the mouth prior to ingestion or ingested in solution.

3 Claims, No Drawings

TASTE MASKING FOR UNPLATABLE FORMULATIONS

FIELD OF THE INVENTION

The invention is related to taste masking of ingredients such as pharmaceuticals or nutritionals intended to be dissolved in the mouth or chewed or delivered to the mouth in a liquid form. Examples of such pharmaceutical formulations are a cough syrups, suspensions, or solutions prepared by the dissolution of an effervescent tablet in water prior to ingestion.

BACKGROUND OF THE INVENTION

Many ingredients in pharmaceutical or nutritional formulations are unpalatable in varying degrees. Such ingredients will be referred to herein as "medicinals" and may include vitamins and well as other ingredients not strictly categorized as pharmaceuticals. The preferred mode of ingestion for many individuals is a tablet or capsule, which allows the medicinal to be taken without contract with the mouth. However, at some times, and for some classes of individuals, liquids, chewables, or formulations intended to dissolve quickly in the mouth are preferred. Because of this there is always a search for suitable taste masking components. Cough syrups are often flavored with fruit flavors such as cherry and cough drops may have a fruit or mint flavor along with sucrose or high fructose syrups. Effervescent formulations have particular flavor problems. Such formulations are provided to the consumer in tablet form which requires that tabletting requirements of compressibility and general manufacturability be met. However, the tablet is dissolved in water by the consumer prior to ingestion; and therefore all the problems of the taste of the solution must also be overcome also. Effervescent formulations have generally been flavored by one of the citrus flavorings, such as orange or lemon/lime.

SUMMARY OF THE INVENTION

The invention provides a taste masking composition useful in medicinal formulations. The taste masking composition is composed of clove oil and either a supportive flavor component or calcium carbonate. The taste masking composition is useful for medicinal formulations intended to dissolve in the mouth or be chewed; or with medicinal formulations in liquid form when taken into the mouth, such as syrups, suspensions or solutions prepared with effervescent tablets. The taste masking composition provided herein is particularly useful with cough/cold formulations which may include one or more of an analgesic, expectorant, antitussives, antihistamine or decongestant. A preferred supportive flavor component is a vanilla flavor. Calcium carbonate may also be used in conjunction with clove oil.

DETAILED DESCRIPTION OF THE PREFERRED EMBODIMENTS OF THE INVENTION

Clove oil has been found to be a particularly good taste masking component to mask the bitter taste of a number of medicinals, particularly analgesics, expectorants, antitussives, decongestants or combinations thereof. Clove oil is spicy and has a slight anesthetic effect, which has proved very effective in masking the bitter taste notes of such medicinals. Other flavors may be used to support the taste masking capabilities of clove. Vanilla flavoring, such as honey or artificial vanilla, are preferred. With particularly bitter medicinals, such as acetaminophen, the slight chalky taste of calcium carbonate was a useful addition to the taste masking composition and improved the general palatability of acetaminophen containing formulations. It was particularly useful with effervescent formulations, although the resulting solution was slightly hazy.

The clove oil used herein was spray dried, although other forms suitable for use in medicinal formulations will be available to those of ordinary skill in the art. The clove oil may be used in the range of 0.045% to 0.097%, calculated as the weight percent of clove oil per tablet. The supportive flavor component is generally used in a range less than or equal to the weight range of the clove oil. Calcium carbonate, when used in effervescent formulations, is generally used in the range of 2.40 or 9.7%. The clove to calcium carbonate ratio in effervescent tablets is generally from about 2.5 to 3.5 weight percent. Additional flavor components may be used to support the clove oil or clove oil/calcium carbonate combination. Preferred are vanilla flavors, such as honey vanilla and artificial vanilla, available from Firmenich, located at Plainsboro, N.J. However, other flavors are well known and available to those of ordinary skill in the art.

Generally, medicinals are unpalatable, often bitter. However, this taste masking composition may be used with medicinal formulations even if the flavoring requirements are not particularly stringent. Such unpalatable components may be in any drug category. Particular examples well known to those of ordinary skill in the art are analgesics such as acetaminophen, acetylsalicylic acid, ketoprofen and the like, $H_2$ Blockers, and most expectorants and decongestants. Antibiotics may also benefit from the addition of this taste masking composition. Formulations which are intended to be chewed or dissolve in the mouth are well known. Many vitamin formulations are chewable. Formulations designed to disintegrate in the mouth are disclosed in U.S. Pat. Nos. 5,225,197 to Beecham and 5,223,264 to Cima. The number of formulations designed to dissolve rapidly in the mouth is increasing. Two such formulations are disclosed in U.S. Pat. No. 5,501,858 (to Fuisz) and U.S. Pat. No. 4,642,903 (to RP Scherer). In any of these forms, the exposure of the medicinals in the mouth may require additional taste masking even if the medicinal is encapsulated to decrease its direct contact with taste buds.

Effervescent formulations are also well known to those of skill in the art. Such formulations are disclosed in U.S. Pat. Nos. 3,495,001; 3,518,344; 4,083,950; 4,783,331; and 4,942,039, all assigned to Miles. The formulations include an effervescent couple composed of an edible organic acid, often citric acid, and a bicarbonate or carbonate, such as sodium bicarbonate. Other components, well known to those of skill in the art of effervescent tabletting may also be used as required to produce suitable tablet quality. Examples of such additional components are lubricants, sweeteners, if desired, excipients, clarity enhancing components and others, such as sorbitol and mannitol to enhance compressibility. Specific components and the proportions of use may be found in many publically available documents.

EXAMPLES

Example 1: Cough/Cold Effervescent Formulation

| Ingredient | mg/Tablet |
|---|---|
| medicinals: | |
| Chlorpheniramine maleate | 2 |
| Dextromethorphan Hydrobromide | 10 |
| Phenylpropanolamine bitartrate | 21 |
| Fuafenisin | 100 |
| effervescent components: | |
| citric acid, anhydrous milled | 800 |
| sodium bicarbonate | 650 |
| taste masking composition: | |
| natural clove flavor | 8.5 |
| honey vanilla flavor | 5 |
| calcium carbonate, SD | 250 |
| other | |
| clarifying agents | 2 |
| lubricants | 67.5 |
| artificial sweeteners | 25 |
| sorbitol | 200 |
| mannitol, milled | 800 |

Compritol HD5-ATO, available from Gattefosse, located at Westwood, N.J., is used as a lubricant along with fumaric acid. The clarifying agents are a blend of providone, surfactant and an antifoaming agent. Useful artificial sweeteners include aspartame and asulfame K. The latter is available from Hoechst Food Ingredients, Sommerset, N.J.

To prepare the tablets, the medicinal components, effervescent couple, mannitol, sorbitol and calcium carbonate are weighed and sized twice through a 20 mesh screen. The screened mixture is blended in a V blender (PK Twin Shell). The taste masking composition and clarifying agents are then weighed and screened separately and added to the blended medicinals and mixed. Finally the lubricating agents are weighed, sized, added to the previously blended ingredients and mixed. This final blend is then compressed to produce the desired tablets.

This effervescent tablet may be dissolved in hot or cold water prior to ingestion. Generally it is dissolved in approximately 4 oz of water and provides good palatability. For effervescent tablets, it has been found useful to calculate the amount of organic acid in the effervescent couple, in this case citric acid, to provide a pH between 4.9 and 5.4 in the final solution (after dissolution of the tablet in about 120 ml water for ingestion).

Example 2: Analgesic Cough/Cold Effervescent Formulation

| Ingredient | mg/Tablet |
|---|---|
| medicinals: | |
| Chlorpheniramine maleate | 2 |
| Dextromethorphan Hydrobromide | 10 |
| Phenylpropanolamine bitartrate | 21 |
| Guafenisin | 100 |
| Acetaminophen (90%) | 361 |
| effervescent component: | |
| citric acid, anhydrous milled | 900 |
| sodium bicarbonate | 650 |
| taste masking composition: | |
| natural clove flavor | 9 |
| honey vanilla flavor | 7 |
| N & A tea flavor | 7 |
| calcium carbonate, SD | 300 |
| other | |
| clarify agents | 2 |
| artificial sweeteners | 29 |
| lubricating agents | 67.5 |
| sorbitol | 200 |
| mannitol, milled | 500 |

Tablets are prepared and compressed as discussed previously. This effervescent tablet may be dissolve in hot or cold water prior to ingestion. Generally it is dissolved in approximately 4 oz of water and provides good palatability.

Example 3: Analgesic Sleep-Aid in an Effervescent Formulation

| Ingredient | mg/Tablet |
|---|---|
| medicinals: | |
| acetysalicylic acid | 338 |
| diphenhydramine citrate | 40 |
| taste masking composition: | |
| artificial vanilla flavor | 1 |
| N & A tea flavor | 1 |
| natural clove flavor | 1.5 |
| effervescent couple: | |
| sodium bicarbonate | 1700. |
| citric acid, anhydrous milled | 1000. |
| other | |
| artificial sweeteners | 7.5 |
| clarifying agents | 2 |

The effervescent tablets are prepared as described above. This effervescent tablet provides both analgesic and sleep-aid components.

Although calcium carbonate could be added, in this case it was omitted to provide a particularly clear liquid after dissolution in water.

Obviously many modifications and variations of the invention as set forth may be made without departing from the spirit or scope of the invention which is defined by the claims herein.

What is claimed is:

1. An effervescent formulation, comprising:
   a) an effervescent couple;
   b) acetylsalicylic acid;
   c) a soluble diphenhydramine salt;
   d) clove oil; and
   e) a supportive flavor component.
2. An effervescent formulation; comprising:
   a) an effervescent couple;
   b) an expectorant;
   c) an antihistamine;
   d) a decongestant;
   e) clove oil; and
   f) calcium carbonate.
3. The effervescent formulation of claim 2 additionally comprising: acetaminophen.

* * * * *